(12) United States Patent
Deshpande (10) Patent No.: US 8,870,769 B2
(45) Date of Patent: Oct. 28, 2014

(54) INTER DIALYTIC MONITORING DEVICE

(75) Inventor: Manish Deshpande, Canton, MA (US)

(73) Assignee: Covidien LP, Mansfield, MA (US)

( * ) Notice: Subject to any disclaimer, the term of this patent is extended or adjusted under 35 U.S.C. 154(b) by 777 days.

(21) Appl. No.: 13/113,175

(22) Filed: May 23, 2011

(65) Prior Publication Data

US 2012/0302848 A1 Nov. 29, 2012

(51) Int. Cl.
*A61B 5/05* (2006.01)
*A61B 5/15* (2006.01)
*A61B 5/145* (2006.01)
*A61B 5/155* (2006.01)
*A61M 1/36* (2006.01)
*A61B 5/00* (2006.01)

(52) U.S. Cl.
CPC .......... *A61B 5/1427* (2013.01); *A61M 2230/20* (2013.01); *A61B 5/150755* (2013.01); *A61B 2560/0443* (2013.01); *A61B 5/14528* (2013.01); *A61B 5/15003* (2013.01); *A61B 5/6852* (2013.01); *A61B 2562/0295* (2013.01); *A61B 5/6866* (2013.01); *A61M 1/3609* (2013.01); *A61M 2230/30* (2013.01); *A61B 5/155* (2013.01); *A61B 5/150992* (2013.01)
USPC ........................................................ 600/365

(58) Field of Classification Search
USPC ................................. 600/345, 347, 365, 309
See application file for complete search history.

(56) References Cited

U.S. PATENT DOCUMENTS

| | | | |
|---|---|---|---|
| 4,925,268 A | 5/1990 | Iyer et al. | |
| 5,000,901 A | 3/1991 | Iyer et al. | |
| 5,127,077 A | 6/1992 | Iyer et al. | |
| 5,368,029 A | 11/1994 | Holcombe et al. | |
| 7,006,858 B2 | 2/2006 | Silver et al. | |
| 7,181,261 B2 | 2/2007 | Silver et al. | |
| 7,615,007 B2 | 11/2009 | Shults et al. | |
| 7,769,420 B2 | 8/2010 | Silver et al. | |
| 7,775,975 B2 | 8/2010 | Brister et al. | |
| 7,828,728 B2 | 11/2010 | Boock et al. | |
| 2007/0027385 A1* | 2/2007 | Brister et al. ................. | 600/365 |
| 2007/0083091 A1* | 4/2007 | Sterling et al. ................ | 600/300 |
| 2007/0225675 A1* | 9/2007 | Robinson et al. ............. | 604/504 |
| 2008/0086044 A1* | 4/2008 | Brister et al. ................. | 600/365 |
| 2008/0091166 A1 | 4/2008 | Fitzgerald et al. | |
| 2008/0119703 A1 | 5/2008 | Brister | |
| 2008/0176271 A1 | 7/2008 | Silver et al. | |
| 2008/0214909 A1* | 9/2008 | Fuerst et al. ................. | 600/309 |
| 2008/0249388 A1 | 10/2008 | Kumhyr | |
| 2009/0187131 A1 | 7/2009 | Fitzgerald et al. | |
| 2009/0227952 A1 | 9/2009 | Blakstvedt et al. | |

(Continued)

FOREIGN PATENT DOCUMENTS

| | | |
|---|---|---|
| DE | 44 05 149 | 9/1994 |
| DE | 198 58 426 | 9/1999 |

(Continued)

OTHER PUBLICATIONS

Official Action issued in the corresponding Japanese Application No. 2012-116632 dated mailed 2, 2013.

(Continued)

*Primary Examiner* — Michael D'Angelo
(74) *Attorney, Agent, or Firm* — John Paul Mello, Esq.

(57) ABSTRACT

An inter dialytic monitoring device is disclosed which monitors in vivo preselected parameters of blood content during an inter dialytic period to monitor patient health. The monitoring device is configured to extend through and releasably engage a catheter which has been placed within a patient to monitor a patient's blood. A sensor is provided to detect the presence of selected analytes and to identify when preselected parameters have been reached.

19 Claims, 5 Drawing Sheets

(56) References Cited

U.S. PATENT DOCUMENTS

| | | |
|---|---|---|
| 2010/0010328 A1 | 1/2010 | Nguyen et al. |
| 2010/0072994 A1 | 3/2010 | Lee et al. |
| 2010/0331644 A1 | 12/2010 | Neale et al. |

FOREIGN PATENT DOCUMENTS

| | | |
|---|---|---|
| WO | WO 2005/033701 | 4/2005 |
| WO | 2006029293 A1 | 3/2006 |
| WO | WO 2010/103051 | 9/2010 |
| WO | WO 2010/118150 | 10/2010 |

OTHER PUBLICATIONS

Australian Examination Report dated Nov. 9, 2012 in copending Australian Appln. No. 2012202682.

European Search Report dated Sep. 19, 2012 in copending European Application No. 12167495.6.

* cited by examiner

INTER DIALYTIC MONITORING DEVICE

BACKGROUND

1. Technical Field

The present disclosure relates to devices for monitoring a patient's health during inter dialytic periods. More specifically, the present disclosure relates to in-vivo monitoring devices for identifying selected physical parameters of interest relevant to patient health and dialysis needs during inter dialytic periods.

2. Background of Related Art

Dialysis or hemodialysis is a procedure used to provide an artificial replacement for lost or reduced kidney function in people with renal failure. Hemodialysis may be used for those with acute disturbance in kidney function as well as those with chronic kidney disease. Those with chronic kidney disease or chronic renal failure require hemodialysis at regular intervals until a renal transplant can be performed.

For a patient suffering from lost or reduced kidney function, a hemodialysis procedure is required about three times per week and each procedure takes about 3-5 hours to perform. During a hemodialysis procedure, a patient's blood is withdrawn from the patient through a catheter and is pumped through a dialyzer to expose the blood to a partially permeable membrane formed of synthetic hollow fibers. The blood flows through the fibers as a dialysis solution flows around the outside of the fibers such that water and waste are removed from the blood. The cleansed blood is then returned to the patient through the catheter.

Catheters suitable for performing hemodialysis include single, dual lumen and triple lumen catheters. Prior to use, the catheter is placed within the body of a patient in a known manner and remains in place for extended periods of time. In use, the catheter is connected to a dialyzer and blood is withdrawn through an arterial lumen of the catheter and returned to the patient through a venous lumen of the catheter.

As is obvious, hemodialysis procedures are time consuming and taxing to a patient. Currently, the frequency of hemodialysis procedures is determined based upon past experience and is not necessarily related to the actual condition of a patient's blood. It would be desirable to have a real time monitoring device which is usable during the inter dialytic period to identify exactly when hemodialysis treatment is necessary to minimize the frequency of dialysis treatments or, in the alternative, ensure that dialysis treatment is provided when needed. It would also be desirable to have a real time monitoring device for monitoring other parameters of interest related and unrelated to dialysis, such as blood pressure, glucose levels, thrombus formation, and infection, relevant to patient heath.

SUMMARY

The present disclosure relates to embodiments of an inter dialytic monitoring device. In one embodiment, the device which comprises a sensory wire configured and dimensioned to extend through a lumen of a catheter. The sensory wire has a tip positioned to be exposed to blood flow within a patient. A sensor is operably associated with the sensory wire and is adapted to detect the presence of a preselected analyte within a patient's blood. An indicator is operably associated with the sensor and is configured to provide an indication to a patient that preselected parameters have been reached regarding the preselected analyte.

In one embodiment, an ion-selective membrane is provided which covers the tip of the sensory wire and is permeable to specific preselected analytes. The sensor may be supported on the tip of the sensory wire and covered by the ion-selective membrane.

In one embodiment, the indicator includes a light which illuminates when the preselected parameters have been reached. The indicator may include a first light and a second light, wherein the first light is illuminated when the preselected parameters have not been reached and the second light is illuminated when the preselected parameters have been reached. The first light may be green and the second light may be red.

In one embodiment, the sensory wire defines a microchannel extending from the tip of the sensory wire to the sensor and back to the tip and the sensor is supported on an end of the sensory wire opposite to the tip. The microchannel may include a fluid, such as saline, which is circulated through the microchannel between the tip and the sensor.

In one embodiment, the sensor and the indicator are supported in a sensor device which is connected to the end of the sensory wire opposite to the tip. The end of the sensory wire opposite to the tip may include a port for removably receiving the sensor device. In one embodiment, the sensor device includes a body and a removable cartridge, wherein the body defines a cavity for receiving the removable cartridge. The removable cartridge may be configured to support the sensor. The fluid circulating in the microchannel may be contained within the removable cartridge. In such a device, the cartridge may be disposable and the body of the sensor device which supports the indicator may be reusable.

In one embodiment, the sensor device includes removable test strips.

In one embodiment, the preselected analyte is selected from the group consisting of glucose, sodium, potassium, urea, hematocrit, and oxygen saturation.

The monitoring device may include a connector for securing the monitoring device to a catheter. In addition, the sensory wire may be adapted to be conducive to clot formation.

In one embodiment, the body includes the mechanical and electrical components to pump fluid through the microchannel and to translate signals received from the sensor.

BRIEF DESCRIPTION OF THE DRAWINGS

Various embodiments of the present disclosure will be described herein with reference to the accompanying drawings, wherein:

FIG. 6 is a side view of the inter dialytic monitoring device shown in FIG. 5 assembled and extending through a catheter shown in phantom; and.

FIG. 7 is a front view of the sensor device of the inter dialytic monitoring device shown in FIG. 5 with the cartridge separated from the body of the monitoring device.

DETAILED DESCRIPTION OF THE EMBODIMENTS

Various exemplary embodiments of the presently disclosed inter dialytic monitoring device will now be described in detail with reference to the drawings wherein like reference numerals identify similar or identical elements in each of the several views.

Figure 1:
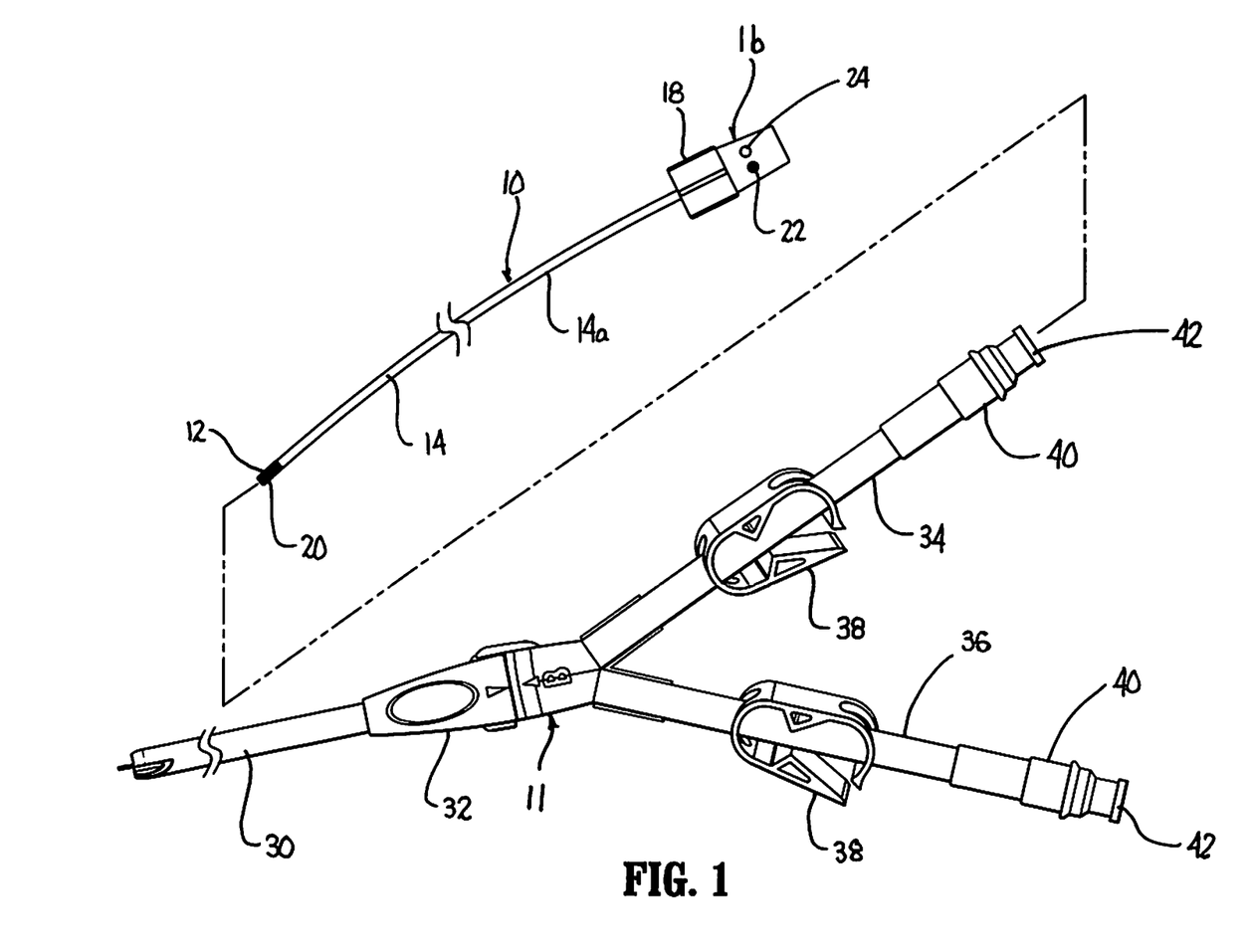
FIG. 1 is a top perspective view of one embodiment of the presently disclosed inter dialytic monitoring device positioned adjacent a catheter.

FIG. 1 illustrates one embodiment of the presently disclosed inter dialytic monitoring device, hereinafter monitoring device 10, prior to insertion of monitoring device 10 within a catheter 11. Monitoring device 10 includes a sensor 12, a sensory wire 14, an indicator assembly 16, and a connector 18.

Figures 2, 3:
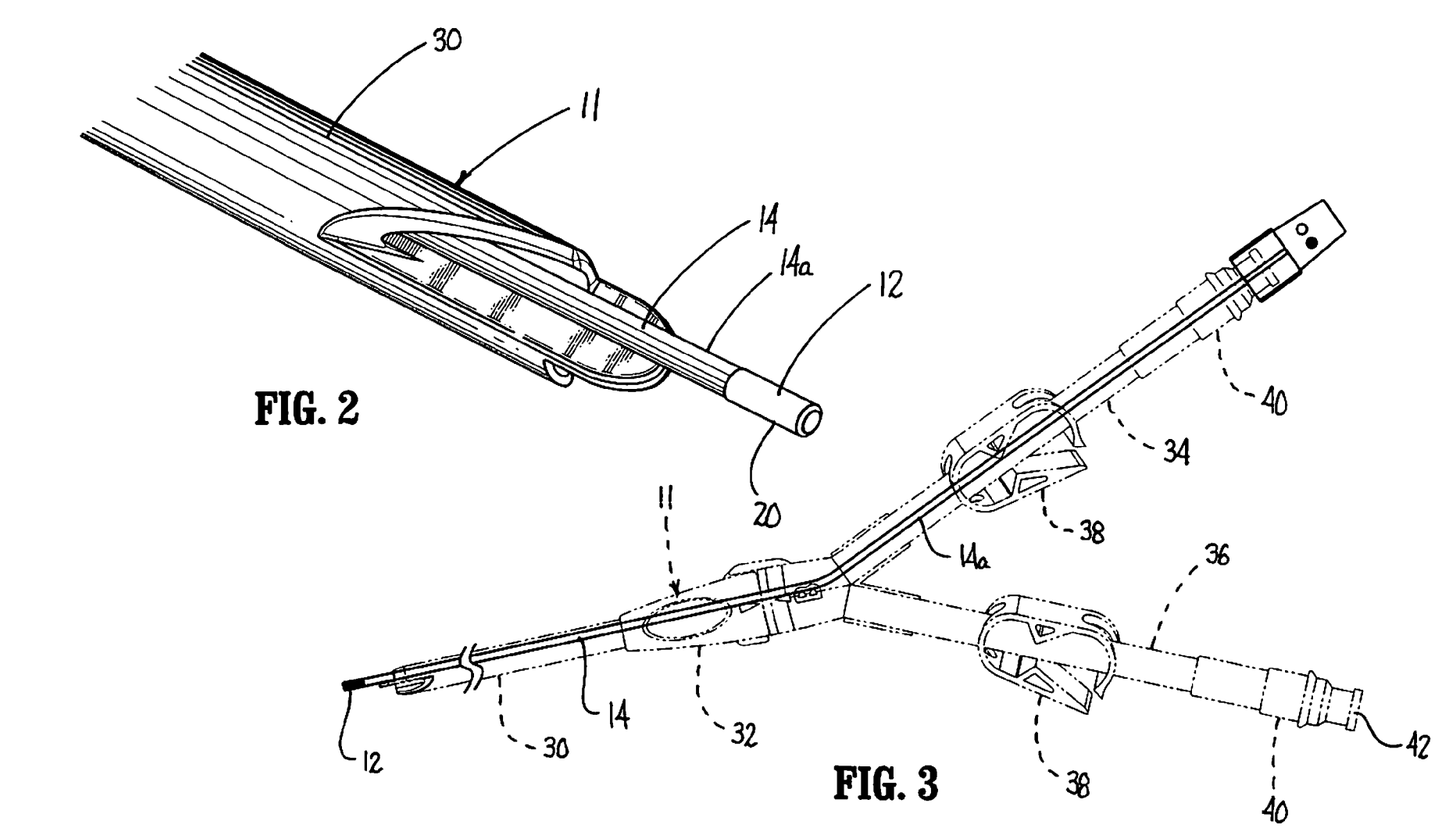
FIG. 2 is a side perspective view of the distal end of a catheter with the presently disclosed inter dialytic monitoring device shown in FIG. 1 extending from the distal end of a catheter lumen of the catheter.
FIG. 3 is a top perspective view of the presently disclosed inter dialytic monitoring device shown in FIG. 1 positioned within a catheter shown in phantom.

Sensory wire 14 includes a first end connected to the sensor 12 and a second end connected to the indicator assembly 16. The sensory wire 14 is dimensioned to be received within and extend through a lumen of a catheter 11 such that the sensor 12 is exposed to blood flow within a body lumen. In one embodiment, as shown in FIGS. 2 and 3, the sensory wire 14 is of a length to position the sensor 12 externally of the catheter 11 to facilitate blood flow across or over the sensor 12. Alternatively, in catheters configured to allow blood flow within the forward ends of the catheter lumens, the sensory wire 14 can be of a length to position the sensor 12 within the catheter lumen adjacent the forward end of the catheter lumen. In one embodiment, the sensory wire 14 defines a flexible electrical circuit and is encased in an elastomeric shell 14a. The elastomeric shell 14a provides a compressible surface for allowing a seal to be effected about the sensory wire 14 as will be discussed below.

The sensor 12 is mounted on the first end of the sensory wire 14 and is electrically connected to the indicator 16 which is mounted on the second end of the sensory wire 14. The sensor 12 may be a single use sensor or a multiple use sensor. The sensor 12 may be a conductivity, optical, or electrochemical sensor. In addition, the sensor 12 may be used to identify analytes including glucose, sodium, potassium, urea, hematocrit, oxygen saturation or other parameters relevant to patient health. In one embodiment, an ion-selective membrane 20 is positioned about and covers the sensor 12. The ion-selective membrane 20 selected is, for example, specific to the analyte of interest and thus, is permeable to a particular analyte. For example, the ion-selective membrane 20 may be specific to glucose, and thus is permeable to glucose ions to allow glucose ions to contact the sensor 12.

As discussed above, the indicator assembly 16 is supported on the second end of the sensory wire 14 and is electrically connected to the sensor 12 by the sensory wire 14. In one embodiment, the indicator assembly 16 supports a battery (not shown) and includes an indicator mechanism which provides a visual and/or audible signal which identifies to a patient and/or medical personnel that a particular preselected parameter as measured by the sensor 12 is present in a patient's blood. In one embodiment, the indicator mechanism may include a red light 22 and a green light 24. In normal use, the green light may be illuminated. When a preselected parameter is sensed in a patient's blood, the red light becomes illuminated to indicate that the preselected parameter has been reached. Alternatively, the indicator assembly may include a single light which illuminates or dims when the preselected parameter has been reached or any of a variety of other audible and/or visual indicators.

As illustrated in FIG. 1, catheter 11 includes a catheter body 30, a catheter hub 32, and first and second extension tubes 34 and 36. Extension tubes 34 and 36 each include a clamp member 38, as known in the art, for selectively sealing a respective extension tube 34 or 36 during the inter dialytic period. An end of each extension tube 34 and 36 opposite the hub 32 supports a connector, e.g., luer connector 40. Caps 42 may be secured to one or both of the extension tubes 34 and 36 to seal the extension tubes 34 and 36 during the inter dialytic period.

During a dialysis procedure, luer connectors 40 facilitate connection of extension tubes 34 and 36 to a dialysis machine. During the inter dialytic period, one of the luer connectors 40 can be used to secure the monitoring device 10 to the catheter 11 as will be discussed in further detail below.

Referring to FIGS. 1 and 3, the indicator assembly 16 supports a luer connector 18 which is positioned and configured to releasably engage one of the luer connectors 40 of extension tubes 34 or 36 to secure the monitoring device 10 to the catheter 11. When the monitoring device 10 is secured to the catheter 11, luer connector 18 is secured to a luer connector 40, sensory wire 16 extends through a respective extension tube 34 or 36 and a lumen of catheter body 30, and sensor 12 is positioned adjacent the end of catheter body 30 opposite catheter hub 32. As discussed above, sensor 12 is positioned to be exposed to blood flow and may extend from or be positioned with a catheter lumen.

In one embodiment, the diameter of sensory wire 14 or elastomeric shell 14a can be selected to prevent clotting within the catheter 11, i.e., the outer diameter of the sensory wire 14 or elastomeric shell 14a may closely correspond in diameter to the inner diameter of the catheter lumen. Alternatively, the external surface of the sensory wire 14 or elastomeric shell 14a may be configured to be conducive to clot formation. As such, when the monitoring device 10 is removed from the catheter 11 after the inter dialytic period, clots formed on sensory wire 14 or elastomeric shell 14a are also removed from the catheter 11.

After a dialysis procedure has been completed and the luer connectors 40 of extension tubes 34 and 36 have been disconnected from a dialyzer, the monitoring device 10 can be secured to the catheter 11 to provide real time information regarding a patient's need for dialysis, or regarding other parameters of interest related to patient health. To secure monitoring device 10 to catheter 11 after a dialysis procedure has been completed, sensory wire 14 is inserted through one of the extension tubes 34 and 36 and through body 30 of the catheter 11 such that sensor 12 is positioned adjacent the end of catheter body 30 opposite catheter hub 32. As discussed above, if the catheter 11 is configured to permit blood flow within the end of body 30 of catheter 11, sensor 12 can be positioned within the lumen of the catheter 11 at a position to be exposed to blood flow. When sensor 12 is properly positioned, luer connector 18 of indicator assembly 16 is secured to luer connector 40 of a respective extension tube 34 or 36. The other extension tube can be capped during the inter dialytic period and each of clamps 38 can be closed in a known manner to seal the respective extension tube 34 or 36. As discussed above, the sensory wire 14 may be encased in an elastomeric shell 14a which enables clamp 38 to form an effective seal around the sensory wire 14 without damage to the sensory wire 14.

During the inter dialytic period, the sensor 12 is maintained in contact with blood flow within a patient's body to monitor, for example, a preselected analyte, such as glucose, sodium, potassium, urea, hematocrit, oxygen saturation, or other such analytes. As discussed above, an ion selective membrane 20 is positioned about the sensor 12 and is permeable to a selected analyte. When the sensor 12 determines that a selected parameter has been reached, e.g., increased level of urea within the blood, a signal is sent from the sensor 12 via the sensory wire 14 to the indicator assembly 16. When the signal is received by the indicator assembly 16, an appropriate audible and/or visual indicator is activated to indicate to the patient and/or medical personnel that a patient treatment is required, such as further dialysis treatment is necessary or will be necessary in a short period of time.

Prior to performance of a dialysis treatment, the monitoring device 10 can be removed from the catheter 11 by disconnecting luer connector 18 from luer connector 40 and withdrawing the sensory wire 14 from the catheter lumen. Thereafter, the monitoring device 10 can be safely disposed of or disinfected for reuse.

Figure 4:
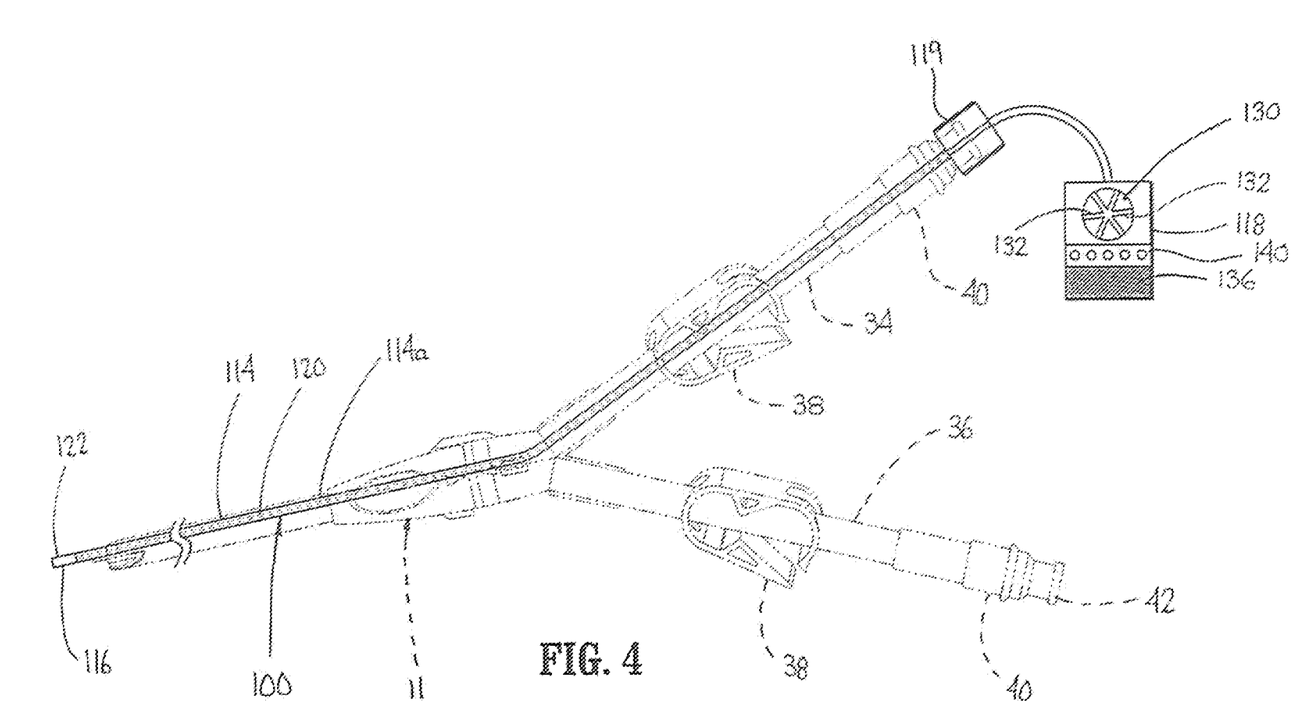
FIG. 4 is a top perspective view of another embodiment of the presently disclosed inter dialytic monitoring device positioned within a catheter shown in phantom.

FIG. 4 illustrates an alternate embodiment of the presently disclosed monitoring device 100 secured to a catheter 11 shown in phantom. Monitoring device 100 includes a sensory wire 114 having a tip 116, a sensor device 118 connected to an end of the sensory wire 114 opposite to the tip 116 and a luer connector 119 secured to the sensory wire 114 near the sensor device 118. The sensory wire 116 defines a microchannel 120 which extends from the sensor device 118 to the tip 116 and back to the sensor device 118. A fluid, such as saline, is circulated in the microchannel 120 at a very slow rate as will be discussed in further detail below. As discussed above with respect to sensory wire 14, sensory wire 116 can be enclosed within an elastomeric shell 114a which allows a seal to be formed about the sensory wire 116 by a clamp 38 positioned about an extension tube 34 or 36 of the catheter 11.

The tip 116 of sensory wire 114 is covered by an ion-selective permeable membrane 122. As discussed above with respect to membrane 20, membrane 122 may be specific to an analyte of interest to enable the analytes of interest to pass into the fluid circulating in the microchannel 120. The transfer of analytes into the fluid in the microchannel 120 through membrane 122 is initiated by the fluid flowing in the microchannel 120 at a very slow rate. The exchanged analytes, i.e., the analytes which pass through membrane 122 into the fluid flowing in microchannel 120, travel from the tip 116 of the sensory wire 114 along the microchannel 120 to the sensor device 118, where a sensor located in the sensor device 118 detects the presence of the selected analyte and performs a quantitative measurement of the analyte.

Sensor device 118 may include a replaceable cartridge 130 which contains the fluid which flows through the microchannel 120 and effects the transfer of analytes across the membrane 122. The replaceable cartridge 130 may include a plurality of sub-cartridges or test strips 132 which can be selectively positioned on demand to measure target parameters of the analyte. The sensor device 118 also includes the sensor for detecting the presence of the selected analytes within the cartridge and/or test strips. Unlike the monitoring device 10, monitoring device 100 can be selectively actuated to perform repeated measurements of a particular analyte or of various analytes.

Sensor device 118 also includes a mechanism (not shown) for initiating flow of fluid through the microchannel 120 of the sensory wire 116, for example, a pump such as a peristaltic pump or other fluid pump. In addition, sensor device 118 may include a display 136 for providing a readout of the results and/or a visual or audible indicator 140 for alerting a patient or medical personnel that the preselected parameters have been met. In one embodiment, a wireless transmitter is provided to send a signal to medical personnel when selected parameters are reached.

The sensor device 118 may be ergonomically configured to be comfortably worn on the body of a patient during the inter dialytic period. Connectors (not shown) such as strips, adhesive layers, clips or the like may be provided on or integrally formed with sensor device 118 to facilitate securement of the sensor device 118 to the body of a patient.

As discussed above, analytes of interest may include sodium, potassium, urea, hematocrit, oxygen saturation and other analytes indicative of a patient's health. In use, the monitoring device 100 is secured to a catheter 11 by inserting the sensory wire 116 through one of the extension tubes 34 or 36 and through catheter 11. Thereafter, connector 119 of monitoring device 100 is secured to the luer connector 40 of the respective extension tube 34 or 36 and clamps 38 are closed to clamp and seal the extension tubes 34 and 36. The sensor device 118 is activated to initiate fluid flow from the cartridge 130 into the microchannel 120 of the sensory wire 116, such that fluid is circulated in the microchannel 120 between the sensor device 118 and the tip 116. As this occurs and fluid flows past the ion-selective membrane 122, selected analytes from a patient's blood are transferred or drawn into the fluid flow within the microchannel 120 and supplied to the cartridge 130. When the sensor of the sensor device 118 is activated either on demand by a patient or medical personnel or at preselected intervals, the presence of the selected analyte and its concentration is detected and an indication of the concentration is provided on the display 136. In addition, notification may be provided when selected parameters have been reached, either visually or audibly, on indicator 140. Based upon the information included on the display 136, appropriate action can be taken by medical personnel with respect to a patient's health. For example, if the information provided on the display indicates that the detected analyte is within accepted norms, no action need be taken. If however, the analyte detected, e.g., urea, is outside accepted norms, the need for dialysis may be indicated.

Typically, the monitoring device 100 is inserted into a catheter after a dialysis procedure and remains connected to the catheter until the next dialysis procedure is required. After the next dialysis procedure, the monitoring device 100 and the associated cartridge 130 can be replaced with a new monitoring device 100 including a new cartridge 130. Alternatively, the monitoring device 100 can be sterilized and reused and only the cartridge 130 need be replaced.

It is contemplated that different monitoring devices 100 that are selective to different analytes can be used with a patient to allow medical personnel to customize the specific parameters of interest to the patient's needs.

Figure 5:
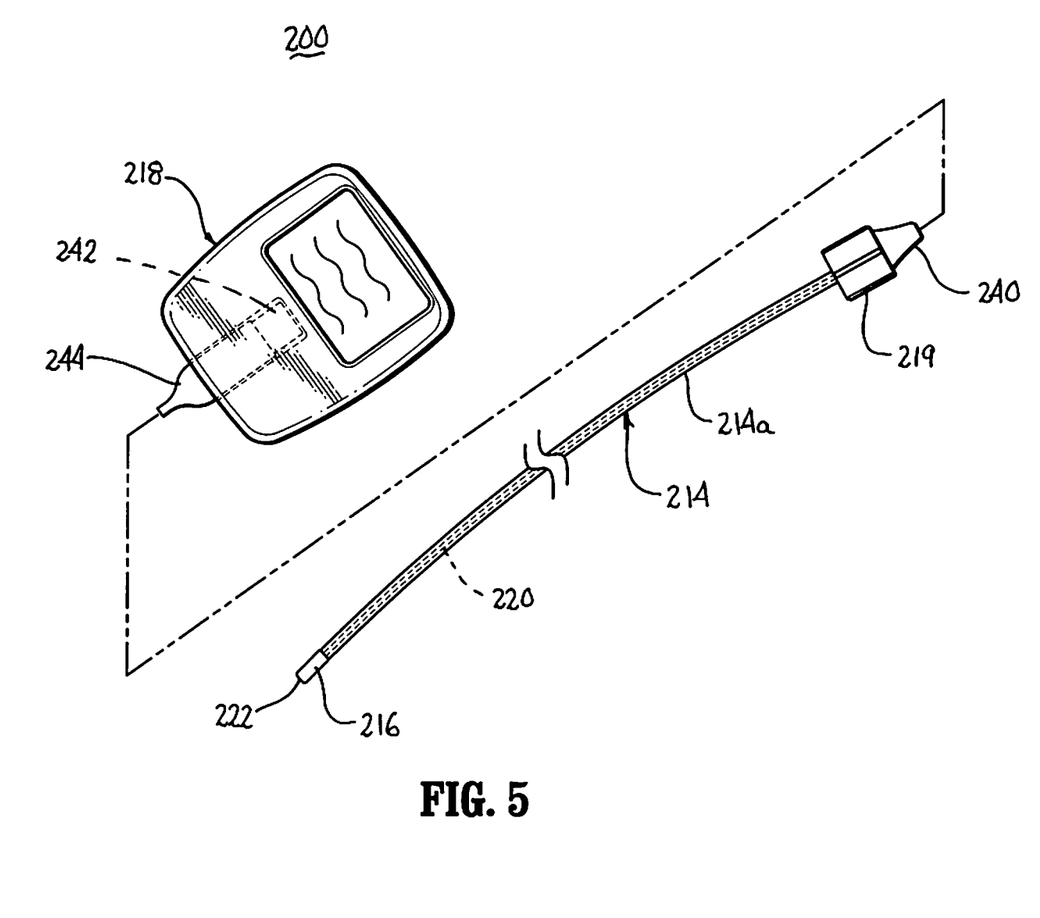
FIG. 5 is a side view of yet another embodiment of the presently disclosed inter dialytic monitoring device with parts separated.
Figures 6, 7:
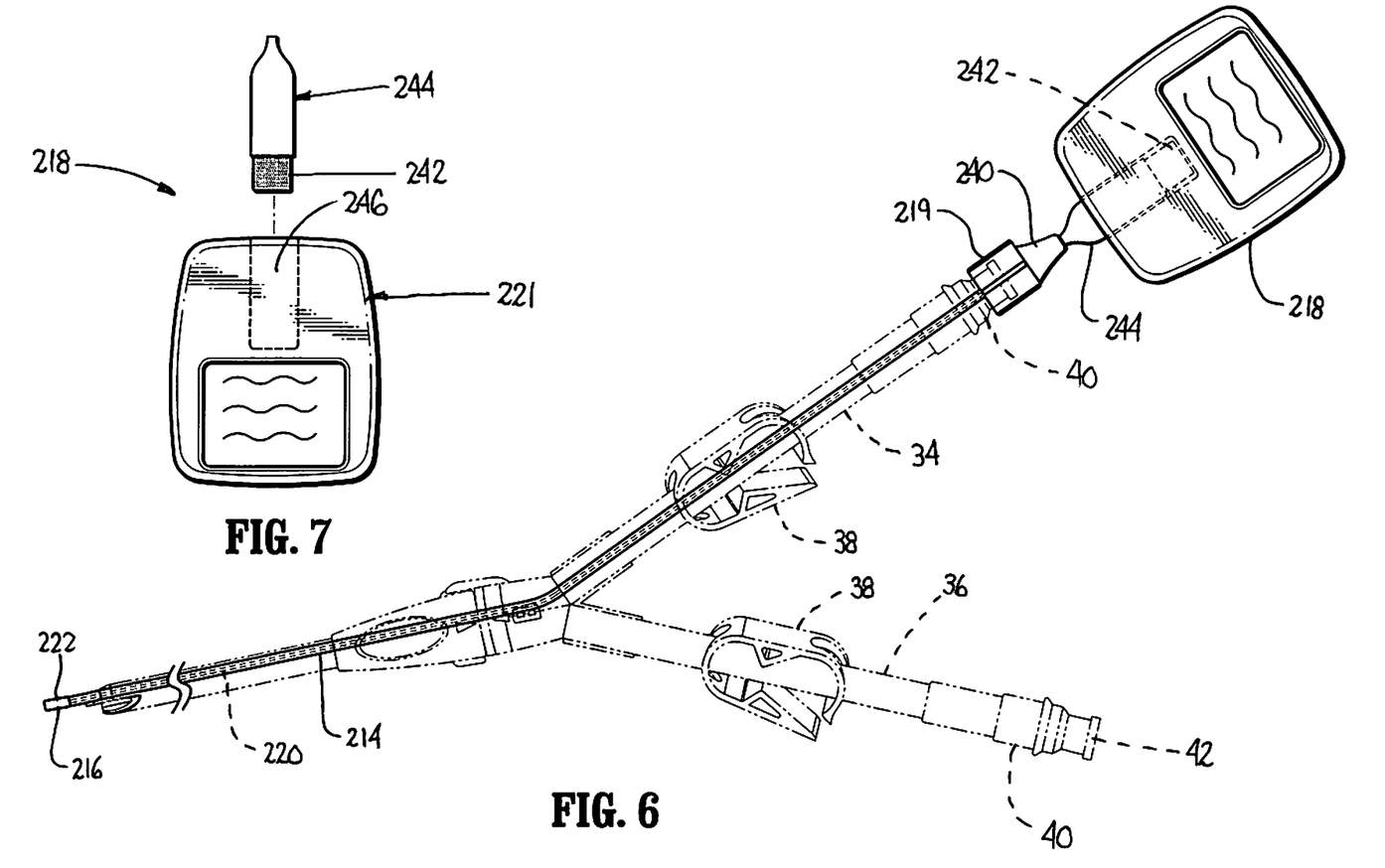

FIGS. 5-7 and 6 illustrate another embodiment of the presently disclosed monitoring device shown generally as 200. Monitoring device 200 is similar to monitoring device 100 and includes a sensory wire 214 having a tip 216 and defining a microchannel 220 and a sensor device 218 located opposite the tip 216. A connector 219 is secured to an end of sensory wire 214 opposite tip 216. An elastomeric shell 214a may be positioned about the sensory wire 214 and an ion-selective permeable membrane 222 covers the tip 216. Monitoring device 200 differs from monitoring device 100 in that sensor device 218 includes a single-use cartridge 244 which is removably engageable with a port 240 located at the end of the sensory wire 214 opposite tip 216, and in that the sensor 242 forms part of the removable single-use cartridge 244 as will be discussed below.

Single-use cartridge 244 is removably received within a receptacle 246 defined within the body 221 of sensor device 218. Cartridge 244 includes sensor 242 and has a first end positioned to be releasably received within port 240 on the end of the sensory wire 214 opposite tip 216. Single-use cartridge 244 may also include the fluid to be circulated through the microchannel of the sensory wire 214, such as saline.

The body 221 of sensor device 218 includes the necessary mechanical and electrical components to pump fluid from the single-use cartridge 244 through the microchannel 220 formed in sensory wire 214 and to provide translation capabilities for translating signals received from the sensor 242. Sensor device 218 also includes a display 248 for providing a visual and/or audible indication of the sensed quantities of interest. Sensor device 218 may also include other visual and/or audibles indicators to indicate or identify to a patient or medical personnel that preselected parameters have been reached.

Monitoring device 200 may include both disposable and reusable components. More specifically, the sensory wire 214 including tip 216, connector 219, and port 240 may be disposable and sensor device 218, excluding single-use cartridge 244 which is disposable, may be reusable. It is noted that because analytes transferred from a patient's blood are transferred to the disposable cartridge 244 and do not contact the remaining components of the sensor device 218, the sensor device 218 may not require sterilization.

While the inter dialytic monitoring device has been described as measuring analytes to determine patient health, the inter dialytic monitoring device may be configured to measure other parameters of interest. For example, the sensor of the inter dialytic monitoring device may be configured to measure microbial formation on or near the catheter to detect infection. Further, the inter dialytic monitoring device may be configured to detect thrombus formation on the catheter, particularly adjacent the distal tip of the catheter.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the system based on the above-described embodiments. Accordingly, the present disclosure is not to be limited by what has been particularly shown and described, except as indicated by the appended claims.

What is claimed is:

1. An inter dialytic monitoring device comprising:
   a sensory wire configured and dimensioned to extend through a lumen of a catheter, the sensory wire having a tip positioned to be exposed to blood flow within a patient, wherein the sensory wire defines a microchannel and the sensor is supported on an end of the sensory wire opposite to the tip, the microchannel extending from the tip to the sensor and back to the tip;
   a sensor operably associated with the sensory wire and being adapted to detect the presence of a preselected analyte within a patient's blood; and
   an indicator operably associated with the sensor configured to provide an indication to a patient that preselected parameters have been reached regarding the preselected analyte.

2. The monitoring device according to claim 1, further including an ion-selective membrane covering the tip of the sensory wire, the ion-selective membrane being permeable to specific preselected analytes.

3. The monitoring device according to claim 2, wherein the sensor is supported on the tip of the sensory wire and is covered by the ion-selective membrane.

4. The monitoring device according to claim 1, wherein the indicator includes a light which illuminates when the preselected parameters have been reached.

5. The monitoring device according to claim 1, wherein the indicator includes a first light and a second light, the first light being illuminated when the preselected parameters have not been reached and the second light being illuminated when the preselected parameters have been reached.

6. The monitoring device according to claim 5, wherein the first light is green and the second light is red.

7. The monitoring device according to claim 1, wherein the microchannel includes a fluid which is circulated through the microchannel between the tip and the sensor.

8. The monitoring device according to claim 7, wherein the fluid is saline.

9. The monitoring device according to claim 7, wherein the sensor and the indicator are supported in a sensor device which is connected to the end of the sensory wire opposite to the tip.

10. The monitoring device according to claim 9, wherein the end of the sensory wire opposite to the tip includes a port for removably receiving the sensor device.

11. The monitoring device according to claim 10, wherein the sensor device includes a body and a removable cartridge, wherein the body defines a cavity for receiving the removable cartridge.

12. The monitoring device according to claim 11, wherein the body includes the mechanical and electrical components to pump fluid through the microchannel and to translate signals received from the sensor.

13. The monitoring device according to claim 11, wherein the removable cartridge supports the sensor.

14. The monitoring device according to claim 12, wherein the fluid circulating in the microchannel is originally contained within the removable cartridge.

15. The monitoring device according to claim 14, wherein the cartridge is disposable and the body of the sensor device which supports the indicator is reusable.

16. The monitoring device according to claim 9, wherein the sensor device includes removable test strips.

17. The monitoring device according to claim 1, wherein the preselected analyte is selected from the group consisting of glucose, sodium, potassium, urea, hematocrit, and oxygen saturation.

18. The monitoring device according to claim 1, further including a connector for securing the monitoring device to a catheter.

19. The monitoring device according to claim 1 wherein the sensory wire is adapted to be conducive to clot formation.

* * * * *